(12) United States Patent
Kowal et al.

(10) Patent No.: US 10,258,229 B2
(45) Date of Patent: Apr. 16, 2019

(54) METHOD FOR THE ACQUISITION OF OPTICAL COHERENCE TOMOGRAPHY IMAGE DATA OF RETINA TISSUE OF AN EYE OF A HUMAN SUBJECT

(71) Applicant: MIMO AG, Bern (CH)

(72) Inventors: Jens Kowal, Seftigen (CH); Gwenolé Quellec, Brest (FR); Peter Maloca, Lucerne (CH)

(73) Assignee: MIMO AG, Berne (CH)

( * ) Notice: Subject to any disclaimer, the term of this patent is extended or adjusted under 35 U.S.C. 154(b) by 128 days.

(21) Appl. No.: 15/309,315

(22) PCT Filed: Apr. 30, 2015

(86) PCT No.: PCT/CH2015/000069
§ 371 (c)(1),
(2) Date: Nov. 7, 2016

(87) PCT Pub. No.: WO2015/168813
PCT Pub. Date: Nov. 12, 2015

(65) Prior Publication Data
US 2017/0071466 A1    Mar. 16, 2017

(30) Foreign Application Priority Data

May 8, 2014 (CH) .......................... 699/14

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/0075* (2013.01);
(Continued)

(58) Field of Classification Search
CPC ..... A61B 3/102; A61B 3/0025; A61B 3/0075; A61B 3/0083; A61B 3/0091; A61B 3/1005; A61B 3/1225; A61B 3/145; A61B 3/152
(Continued)

(56) References Cited

U.S. PATENT DOCUMENTS

| | | | |
|---|---|---|---|
| 6,299,307 | B1 | 10/2001 | Oltean et al. |
| 2005/0024586 | A1 | 2/2005 | Teiwes et al. |

(Continued)

FOREIGN PATENT DOCUMENTS

| | | | |
|---|---|---|---|
| EP | 2 497 414 A1 | 9/2012 | |
| EP | 2 644 085 A1 | 10/2013 | |

(Continued)

OTHER PUBLICATIONS

Office Action dated Jan. 21, 2019 in corresponding Japanese Application No. 2017-510711.

*Primary Examiner* — James Greece
(74) *Attorney, Agent, or Firm* — Birch, Stewart, Kolasch & Birch, LLP.

(57) ABSTRACT

In a method for the acquisition of optical coherence tomography image data of retina tissue of an eye (99) of a human subject using an acquisition device comprising an imaging optics (2), a first image associated with a baseline relative positioning of the eye (99) of the human subject with respect to the imaging optics (2) is acquired at a first point in time. The baseline relative positioning is stored. At a second point in time being different from the first point in time, the baseline relative positioning of the same eye (99) of the same human subject with respect to the imaging optics (2) is re-established and a second image is acquired. For re-establishing the positioning, a present relative positioning of the eye (99) of the human subject with respect to the imaging (Continued)

optics is determined based on a video image of an iris region of the eye. A corresponding device comprises an imaging optics (2), a head support to be contacted by a head portion of the human subject, the head support defining an entrance position of the sample beam entering an eye of the human subject, a camera (71) for acquiring a video image of an iris region of the eye, a display (75) for displaying a target image to the human subject, the target image indicating a direction of a line of vision to be assumed by the human subject, and a processor for determining a present relative positioning of the eye of the human subject with respect to the imaging optics, based on the video image, for comparing a present relative positioning of the eye (99) of the human subject with respect to the imaging optics (2) to a stored baseline relative positioning, for affecting the target image as long as the present relative positioning does not correspond to the stored baseline relative positioning, and for triggering the acquisition of image data when the present relative positioning corresponds to the baseline relative positioning.

11 Claims, 6 Drawing Sheets

(51) Int. Cl.
*A61B 3/00* (2006.01)
*A61B 3/15* (2006.01)
*A61B 3/12* (2006.01)

(52) U.S. Cl.
CPC .......... *A61B 3/0083* (2013.01); *A61B 3/0091* (2013.01); *A61B 3/1005* (2013.01); *A61B 3/1225* (2013.01); *A61B 3/145* (2013.01); *A61B 3/152* (2013.01)

(58) Field of Classification Search
USPC ................................. 351/205–206, 208, 246
See application file for complete search history.

(56) References Cited

U.S. PATENT DOCUMENTS

2007/0252951 A1    11/2007   Hammer et al.
2012/0249956 A1    10/2012   Narasimha-Iyer et al.

FOREIGN PATENT DOCUMENTS

| EP | 2 702 930 A1 | 3/2014 | |
|---|---|---|---|
| EP | 2702930 A1 * | 3/2014 | ............ A61B 3/102 |
| JP | 2012-223428 A | 11/2012 | |
| WO | WO 2008/150330 A1 | 12/2008 | |
| WO | WO 20080150330 A1 * | 12/2008 | ............ A61B 3/113 |
| WO | WO 2010/117386 A1 | 10/2010 | |
| WO | WO 2010117386 A1 * | 10/2010 | ............ A61B 3/102 |

* cited by examiner

METHOD FOR THE ACQUISITION OF OPTICAL COHERENCE TOMOGRAPHY IMAGE DATA OF RETINA TISSUE OF AN EYE OF A HUMAN SUBJECT

TECHNICAL FIELD

The invention relates to a method for the acquisition of optical coherence tomography image data of retina tissue of an eye of a human subject using an acquisition device comprising an imaging optics. It further relates to a device for the acquisition of optical coherence tomography image data of retina tissue of an eye of a human subject.

BACKGROUND ART

Age-related Macular Degeneration (AMD) and especially neovascular AMD (nAMD) is the leading cause of blindness in the developed countries in people ageing over 50 years. An increase in vascular permeability leads to abnormal fluid collection within or below the retina that causes visual dysfunction when it involves the center of the macula. This leads to rapidly deteriorating acuity, scarring of the pigment epithelium, and permanent visual loss or blindness.

However, intravitreal injection of antiangiogenic agents, including Ranibizumab (trade name Lucentis®, Novartis, Basel, Switzerland), has been shown to significantly improve the course of nAMD. To reduce the burden of intravitreal injections and to optimize the risk/benefit profile, the progression of nAMD features can be monitored non-invasively by Optical Coherence Tomography (OCT). Prominent nAMD features involve the increase of the thickness of retinal structures. Such an increase may be identified when visually comparing two OCT images of the same region of the retina taken at different times, the temporal distance being several days to several months.

For instance, patients treated with Ranibizumab usually undergo an OCT examination every month. If a significant growth in nAMD features is observed, then a treatment decision is indicated: the patient receives a Ranibizumab injection that day, one month later and two months later (treatment phase). Retreatment can be indicated one month later if the nAMD features have not completely receded. Otherwise, the patient does not receive an injection that day, but regularly indicated maintenance injections (maintenance phase).

For the OCT acquisition usually sophisticated and correspondingly expensive state-of-the-art OCT devices are employed. They are located at medical offices or specialized units of hospitals. The devices are operated by skilled personnel. This means that the monitored patients are required to visit a medical office or specialized unit of a hospital each time an OCT has to be acquired. This puts a considerable burden upon the patients. Furthermore, the frequency of the OCT acquisitions (such as 1 month) is already sort of a compromise between on one hand close monitoring of the development of nAMD and on the other hand the costs and the burden on the patient.

Firstly, these problems may be alleviated if OCT image acquisition devices are located closer to the patients, in particular if the monitored patients have access to an OCT imaging device at their home. This is only feasible if the OCT devices are compact, comparably inexpensive and may be operated by essentially anyone, most preferably by the patient himself or herself. One problem that has to be solved in that respect is that of acquiring image data covering the whole region of interest of the retina of the human subject. This requires that the examined eye has a certain position and orientation with respect to the optics of the acquisition device. Furthermore, especially if automated analysis of the OCT acquisitions is foreseen, in order to compare images taken at different points in time these images should provide essentially the same view of the examined eye in order to facilitate or even enable the comparison.

However, in connection with state-of-the-art OCT devices usually a skilled operator is required directing the human subject to alter the position of his or her head as well as of the line of vision assumed by the examined eye.

SUMMARY OF THE INVENTION

It is the object of the invention to create a method for the acquisition of OCT image data as well as an OCT imaging device pertaining to the technical field initially mentioned, that are inexpensive and allow for reliable positioning of the eye to be examined.

The solution of the invention is specified by the features of claim 1. According to the invention, the method comprises the following steps:
a) at a first point in time a first OCT image is acquired, associated with a baseline relative positioning of the eye of the human subject with respect to the imaging optics;
b) the baseline relative positioning is stored;
c) at a second point in time being different from the first point in time, the baseline relative positioning of the same eye of the same human subject with respect to the imaging optics is re-established, and a second OCT image is acquired,
where
d) for re-establishing the positioning, a present relative positioning of the eye of the human subject with respect to the imaging optics is determined based on a video image of an iris region of the eye.

In the present context, "video image" refers to one or a plurality of frames representing a visual image, e.g. as captured with a camera having usual active pixel sensors. In particular, a single frame is used for the determination of the relative positioning at the given point in time. However, in principle it is possible to take into account a succession of frames at approximately the point in time of interest.

A video image of the iris region of the eye, i.e. of the anterior segment of the eye (including in particular the cornea, the pupil and the iris and the neighbouring regions of the sclera), may be easily obtained in a very short time, using inexpensive hardware. The video image may be processed by readily available image processing methods and software. Accordingly, the costs of a corresponding imaging device that may be operated without the need for a skilled operator may be minimized. Video images may be taken at fast rates (e.g. 25 or 50 frames/second or more). Accordingly, a fairly recent video image showing the present situation and therefore allowing for quasi-real-time tracking the eye position will always be available. Using near infra-red illumination, negative effects affecting the patient may be minimized.

The baseline relative positioning may be stored on a local storage of the acquisition device or a device connected to the acquisition device. It may as well be stored on a data carrier or transmitted over a network and stored on a server. The baseline relative positioning may be defined by different sets of quantities as shown below.

The inventive method is not restricted to the above mentioned steps. In particular, it may include the further step of actually acquiring OCT image data.

Preferably, the re-establishing step includes an automated repositioning of the imaging optics. The repositioning may be effected along a single or a plurality of axes, where the axes may be linear and/or swivel axes. It may affect the relative positioning of the imaging optics and the eye and/or the relative orientation of these elements.

Advantageously, a head of the human subject is held in a fixed position with respect to a base of the acquisition device and for repositioning the imaging optics is moved with respect to the base. In particular, the imaging optics is held on a unit that is movable with respect to the base and the repositioning is effected by step motors moving the unit to the desired position. In a preferred embodiment, the repositioning is effected along two swivel axes and a Cartesian axis, the latter for setting the distance between the imaging optics and the eye to be examined. Alternatively, the repositioning may be effected along three Cartesian axes, allowing for moving the imaging optics to a predetermined position with respect to the position of the eye.

Preferentially, the re-establishing step includes displaying a target image to the human subject, the target image indicating a direction of a line of vision to be assumed by the human subject. The target image may directly indicate a target for the desired line of vision of the human subject, however it is preferred that the target image is a relative indication providing the human subject with information about how to change the line of vision in order to meet the line of vision to be assumed. The target image may therefore consist of a usual target, indicating a position, e.g. in the form of cross hairs, and/or of an indication of direction such as one or a plurality of arrows.

Preferably, a present relative positioning of the eye of the human subject with respect to the imaging optics is compared to the stored baseline relative positioning. As long as the present relative positioning does not correspond to the stored baseline relative positioning the displayed target image is affected, i.e. the position of the image and/or its shape or size is changed in order to motivate the human subject to change the present line of vision in the direction of the line of vision to be assumed according to the baseline positioning. When finally the present relative positioning corresponds to the baseline relative positioning, the second OCT image is acquired.

Advantageously, a position of the limbus cornae in the video image is determined and used as a reference for the present relative positioning of the eye. It has shown that the position of the limbus may be reliably determined without the need for UV illumination, in particular by using illumination in the near-infrared range. Furthermore, the limbus position is well-defined and the appearance of the limbus is stable, in particular it is not affected by the diurnal change in corneal shape or by pupil dilation. Accordingly, the limbus position provides useful information allowing for determining the position of the retina tissue to be imaged by OCT.

Other location information may be obtained from the video image (e.g. the position of the center of the pupil, the three-dimensional surface of the cornea, iris features or blood vessels on the sclera) and used instead of or in addition to the limbus position.

Preferably, the determination of the present relative positioning of the eye with respect to the imaging optics comprises the step of determining a three-dimensional position and an orientation of the eye.

In a preferred embodiment, the automatic repositioning of the imaging optics as described above takes care of the relative position of the imaging optics with respect to the eye, whereas the interaction of the human subject with the acquisition device, controlled by the target image, takes care of the relative orientation of the imaging optics with respect to the eye.

The orientation is fully described by the three Euler angles. Using the optical axis of the eye as one axis of the corresponding coordinate system, the angles may be referred as torsion angle (rotation about the optical axis of the eye), azimuth and altitude. It has turned out that as long as the head of the human subject is reproducibly positioned with respect to the optical imaging optics, e.g. by using a head support, torsion is not critical and may be neglected. Therefore, in principle two angles (azimuth and altitude) are sufficient for indicating the orientation of the eye.

Preferably, the three-dimensional position and the orientation of the eye are determined by identifying the following quantities:
a) a center of eye rotation; and
b) a normal vector to a limbus plane.

In combination, these two quantities provide the three Cartesian coordinates (i.e. the components of a distance vector) as well as the two angles mentioned before.

Furthermore, they describe the orientation as well as position of the retina, i.e. of the tissue to be imaged. Once these quantities are known no complex calculations are required to establish whether the present relative positioning coincides with the baseline relative positioning.

Advantageously, the determination of the present relative positioning of the eye with respect to the imaging optics comprises the step of determining a center of corneal curvature based on reflected light rays of at least two light sources illuminating the eye, the at least two light sources being spaced from each other.

The center of corneal curvature is a useful starting point for reconstructing the limbus in three dimensions, based on a (two-dimensional) video image of the limbus. The determination using the reflected light rays of the two light sources is inexpensive, fast and reliable.

Advantageously, the inventive method includes the step of determining a radius of corneal curvature of the eye of the human subject by recording video images, simultaneously acquiring OCT images of the cornea to determine a distance of the cornea from the imaging optics, assigning distance values to locations of the video image and determining the radius by a numerical optimization algorithm. The radius of corneal curvature is a quantity that may be used when processing the data obtained from the reflected light rays of the at least two light sources in order to obtain the center of corneal curvature.

It is not necessary to repeat this procedure prior to every acquisition of OCT images as it has turned out that the radius is a stable quantity that does not substantially change with time. Accordingly, in contrast to the determination of the center of corneal curvature the determination of the radius of corneal curvature is basically a calibration step which may be carried out once, in particular when acquiring the first (baseline) image. The resulting value ($\rho$) may be stored together with the baseline relative positioning and used also for later acquisitions.

Advantageously, the method includes the step of determining a distance of the center of eye rotation and a center of corneal curvature of the eye of the human subject. This quantity may be used when finding the center of eye rotation based on the three-dimensional reconstruction of the limbus.

Again, this quantity is stable and does not substantially change with time. Accordingly, it may be carried out once as a calibration step.

Accordingly, in a preferred embodiment, the quantities identifying the three-dimensional position and the orientation of the eye are determined as follows:

A. subject-specific calibration (once, during the acquisition of the baseline image data):
a) determination of the radius of corneal curvature ($\rho$);
b) determination of the distance of the center of eye rotation and a center of corneal curvature (r);

B. determination of the present relative positioning (immediately preceding the actual OCT acquisition process):
c) determination of the center of the corneal curvature (C), based on the reflected light rays of at least two light sources, using the value of $\rho$;
d) reconstruction of the limbus in three-dimensions, based on the video image of the iris region, using the position C;
e) determining a normal vector (n) to a plane defined by the limbus border, based on the limbus reconstruction; and
f) determination of the center of eye rotation (E), based on the limbus reconstruction, using the vector n and the value of r.

A device for the acquisition of optical coherence tomography image data of retina tissue of an eye of a human subject, that is suitable for carrying out the inventive method, comprises
a) an imaging optics;
b) a head support to be contacted by a head portion of the human subject, the head support defining an entrance position of the sample beam entering an eye of the human subject;
c) a camera for acquiring a video image of an iris region of the eye;
d) a display for displaying a target image to the human subject, the target image indicating a direction of a line of vision to be assumed by the human subject;
e) a processor for determining a present relative positioning of the eye of the human subject with respect to the imaging optics, based on the video image, for comparing a present relative positioning of the eye of the human subject with respect to the imaging optics to a stored baseline relative positioning, for affecting the target image as long as the present relative positioning does not correspond to the stored baseline relative positioning, and for triggering the acquisition of image data when the present relative positioning corresponds to the baseline relative positioning.

Preferably, the device comprises a base, the head support is fixed to the base and the imaging optics is movable with respect to the base.

Advantageously, the device comprises an adjustment mechanism for automatically three-dimensionally adjusting a position of the imaging optics with respect to the base.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
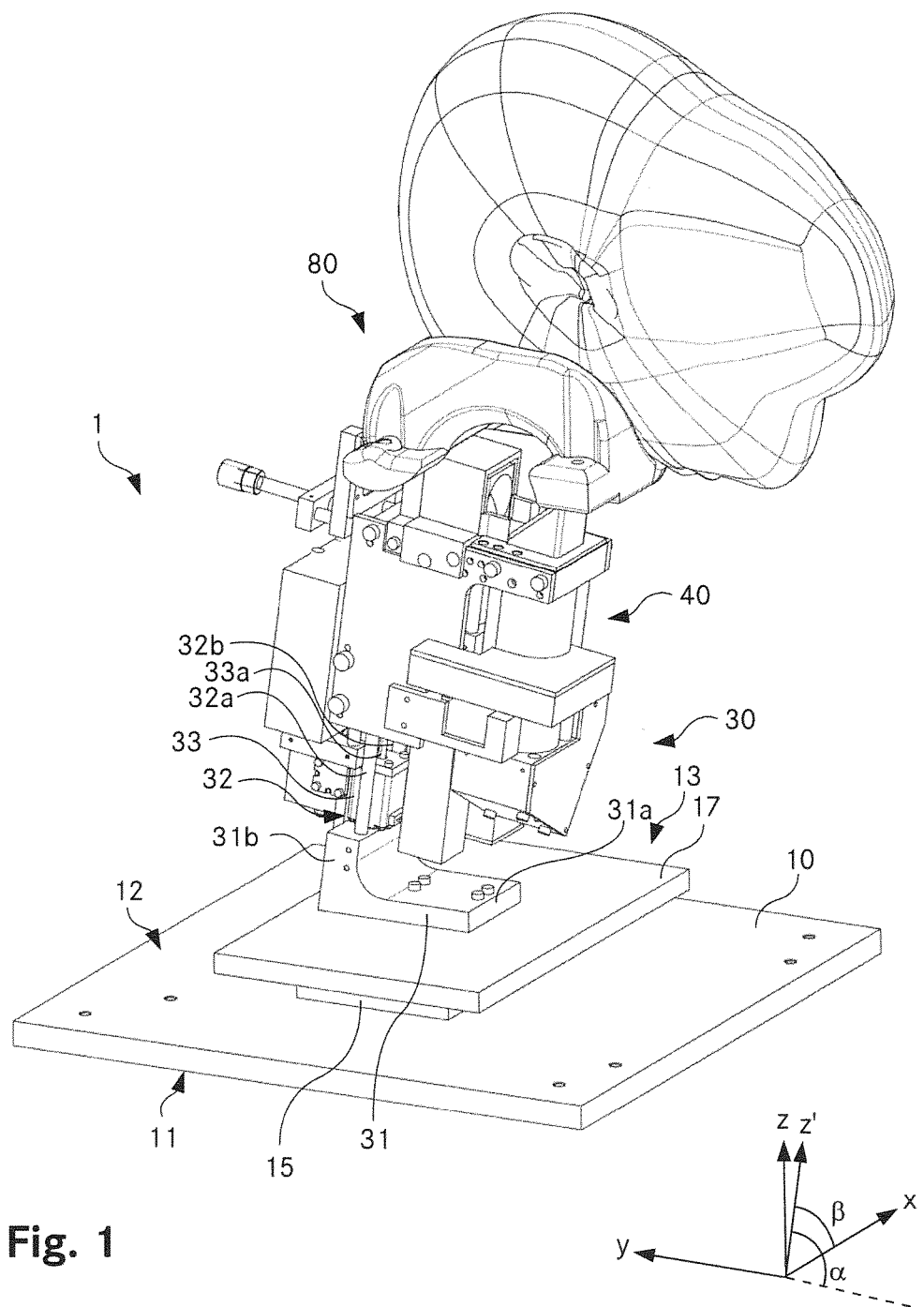
FIG. 1 An articulated view of an OCT device which is adapted to carry out the inventive method.
Figure 2:
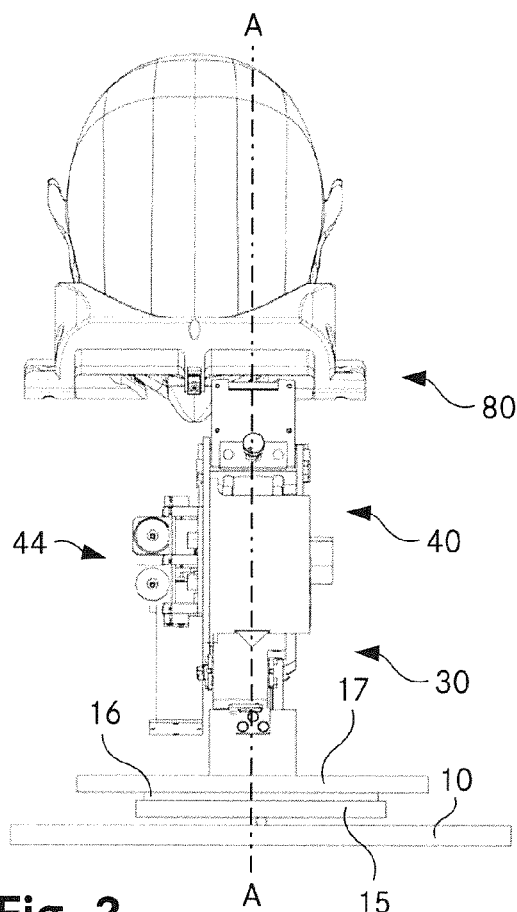
FIG. 2 a frontal view of the OCT device.
Figure 3:
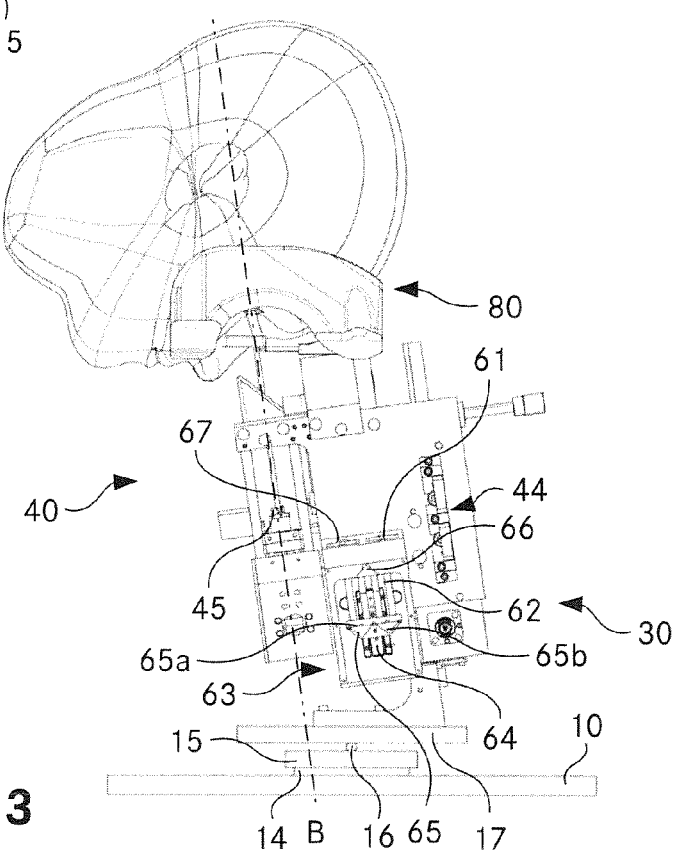
FIG. 3 a side view of the OCT device.
Figure 4:
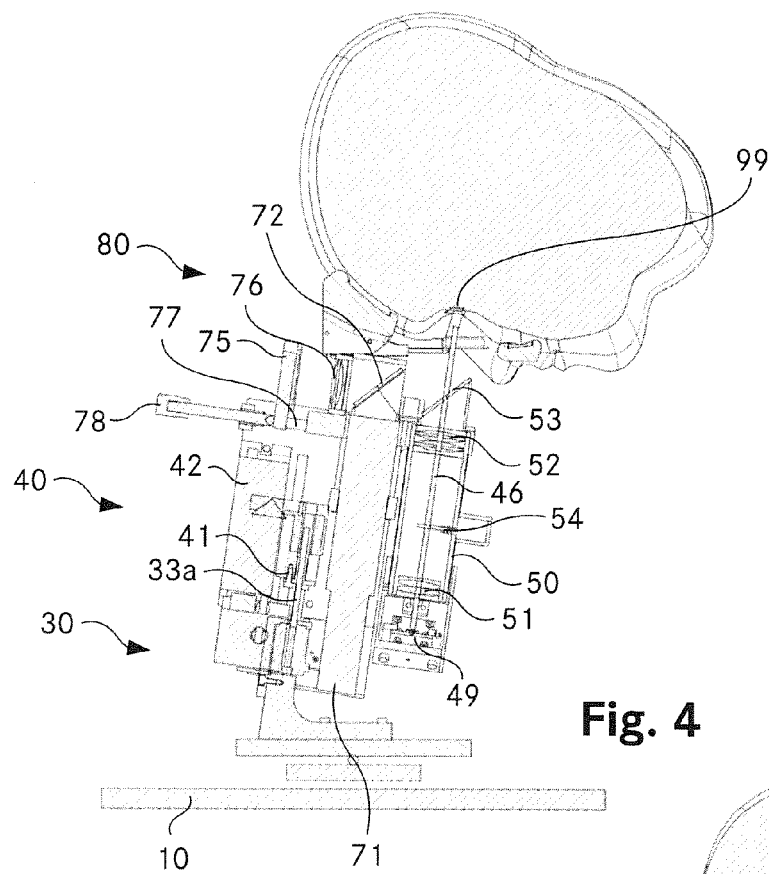
FIG. 4 a cross-sectional view of the OCT device in an yz plane.
Figure 5:
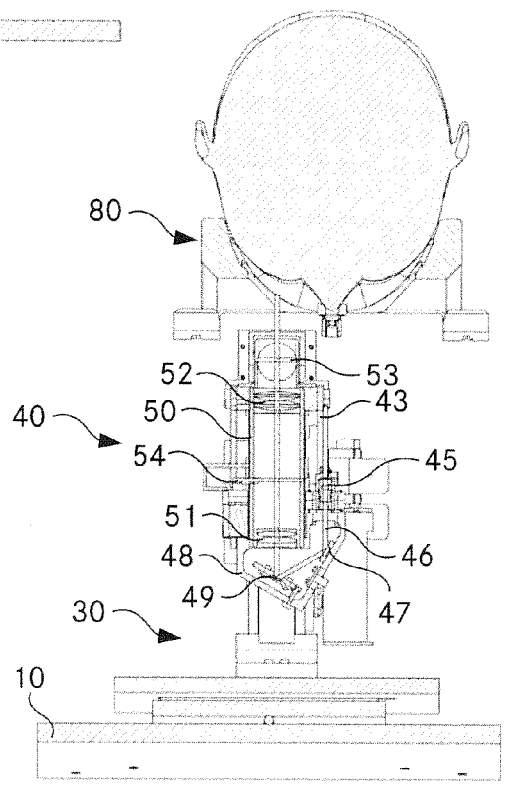
FIG. 5 a cross-sectional view of the OCT device in an xz' plane.

FIG. 1 shows an articulated view of an OCT device which is adapted to carry out the inventive method. FIG. 2 shows a frontal view, FIG. 3 a side view of the OCT device, as seen from the right hand side. FIGS. 4 and 5 show cross-sectional views of the OCT device, FIG. 4 in a yz plane A-A shown in FIG. 2, FIG. 5 in the xz' plane B-B shown in FIG. 3, seen from behind. For simplicity and in order to provide an overview, a housing surrounding the main optical unit as well as a spectrometer has been omitted in the Figures.

The main components of the OCT device 1 are a base plate 10, an optical unit 30 movable mounted to an upper surface of the base plate 10 and a head support 80 arranged above the optical unit 30.

The base plate 10 is rectangular and has uniform thickness. Its size is about 40×40 cm. The base plate 10 comprises a lower surface 11, which is a support surface for the OCT device 1 to be put on a flat surface such as a tabletop, and an upper surface 12 to which the optical unit 30 and the head support 80 are mounted. The head support 80 is mask-like and designated to accommodate a part of the head, contacting a region of the face surrounding the eyes. In the Figures, the mounting of the head support 80 is not shown. However, in principle, the head support 80 may be attached to the upper end of a housing surrounding the optical unit 30.

On the upper surface 12 of the base plate 10 a pivoting mechanism 13 supporting a foot 31 of the optical unit 30 is mounted. The pivoting mechanism 13 allows for pivoting the optical unit 30 about two horizontal pivot axes, the axis running along the x and they direction, both being parallel to the lower and the upper surface 11, 12 of the base plate 10. As can be seen from FIGS. 1-3, the pivoting mechanism 13 comprises a lower pivot axis 14, running in y direction, allowing for adjusting an angle β between the z' axis of the optical unit 30, which corresponds to the direction of the sample beam emitted by the optical unit 30, and the x axis. The lower pivot axis 14 is arranged between the upper surface 12 of the base plate 10 and a lower support plate 15. An upper pivot axis 16, running in x direction, i.e. perpendicular to the lower pivot axis 14, is arranged between the lower support plate 15 and an upper support plate 17. It allows for adjusting the angle α between the z' axis of the optical unit 30 and the y axis. The foot 31 of the optical unit 30 is fixedly attached to the upper support plate 17.

Both pivot axes 14, 16 comprise shafts that are rotatable about their longitudinal axes and which link the two neighbouring elements. The pivoting angle is set by step motors counteracting springs.

The foot 31 of the optical unit 30 is essentially L-shaped, having a first leg 31a extending parallel to the base plate 10 and a second leg 31b connected to the first leg 31a, the first leg 31a and the second leg 31b enclosing an angle α of approximately 82°, depending on the position of the upper pivot axis 16, defining an angle of the axis of the measurement beam with respect to the base 10, as described below. A linear guide 32 is attached to the upper end of the second leg 31b. The linear guide 32 comprises two threaded bars 32a, 32b extending parallel to the second leg 31b and coupled to it in a rotationally fixed manner. The threaded bars 32a, 32b cooperate with threaded nuts rotatably mounted to the upper part 40 of the optical unit 30. A motor 33 is attached to the upper surface of the second leg 31b driving a threaded spindle 33a. This threaded spindle 33a cooperates with a threaded nut 41 fixedly attached to the upper part 40 of the optical unit 30 (see FIG. 4). Using the motor 33 attached to the foot 31, the position of the upper part 40 of the optical unit 30 relative to the z' axis may be adjusted.

The upper part 40 of the optical unit 30 houses the main optical elements of the OCT device 1. The laser light source 42 generating a beam having a wavelength of about 835 nm or higher is housed in a front region of the upper part 40, ahead of the threaded nut 41 and the guide channel for the threaded spindle 33a driven by motor 33 for the z' movement. To the output of the laser light source 42 an optical fiber is connected. The fiber leads to an optical coupler (not shown) where the incoming light beam is split into a measurement beam and a reference beam. The optical coupler may be arranged at the right side of the upper part 40 of the optical unit 30. The measurement beam is coupled into a further optical fiber 43. A section of the latter is coiled up and housed in a coil housing 44 attached to a side wall of the upper part 40, the coil axis lying in the yz plane and being perpendicular to the z' axis. This arrangement allows for controlling the polarization of the measurement beam. The output of the optical fiber 43 is coupled into a collimator 45 comprising a collimator lens. In the shown embodiment, the collimator lens is adapted to monochromatic light and has a focal length of 5.1 mm. A distance between the end of the optical fiber 43 and the collimator lens is adjustable. This allows for adjusting the collimation, in particular the collimation may be chosen to be slightly overdone or slightly incomplete in order to easily compensate hyperopia or myopia of the examined eye, respectively.

The collimated light beam 46 is reflected by a mirror 47 arranged in a first leg of a V-shaped element 48 of the upper part 40 of the optical unit 30. Next, it impinges on a 4-quadrant MEMS mirror 49 in a second leg of the V-shaped element 48. The MEMS mirror 49 has a scanning angle of ±5° and allows for adjusting the direction of the light beam 46 in the x and y directions. Next, the light beam 46 passes a telescope 50 including two lens packages 51, 52 including two lenses each, for projecting the light beam 46 to a pupil of an eye 99 to be examined. In the shown embodiment, all lenses have a diameter of 30 mm, their effective focal length is 100 mm (first lens of the first lens package 51 as well as both lenses of the second lens package 52) and 200 mm, respectively (second lens of the first lens package 51). After passing a dichroic mirror 53 (longpass, 760 nm) the focused light beam 46 enters the eye 99 at an entrance position.

In the described example, the distance between the center of the MEMS mirror 49 and the first lens of the first lens package 51 is 23 mm, the distance between lens packages 51, 52 is 75 mm, the distance between the second lens package 52 and the dichroic mirror 53 is approximately 25 mm, the distance between the center of the dichroic mirror 53 and the entrance position is approximately 43 mm. A plate-shaped blocking element 54 made from aluminium is movably mounted in the region of the telescope 50 and may be inserted by means of actuating an associated drive to block the optical path as well as retracted by the same drive to free the optical path. Blocking the path allows for taking reference measurements for calibration purposes.

Backscattered light of the focused light beam 46 travels back the same optical path, i.e. passes the dichroic mirror 53, is reflected by the MEMS mirror 49 and the mirror 47, is coupled back into the optical fiber 43 and led back to the optical coupler.

At the aforementioned optical coupler, the reference beam is coupled to a further optical fiber which leads to a further collimator 61. The collimated reference beam 62 enters an adjustable reference arm unit 63 arranged at the right side of the upper part 40 of the optical unit 30. The reference arm unit 63 comprises a linear guide 64, running parallel to the reference beam 62, on which a carriage 65 is guided, its position along the guide 64 being precisely adjustable by means of a linear motor. Attached to the carriage 65 are two prisms 65a, 65b for deflecting incoming light by 180°. A third prism 66 is fixedly attached to the reference arm unit 63. Finally, a mirror 67 is also fixedly attached to the reference arm unit 63. The three prisms 65a, 65b, 66 and the mirror 67 are arranged in such a way that the incoming reference beam 62 is deflected by the first prism 65a of the carriage 65, by the third prism 66 fixedly attached to the reference arm unit 63 and by the second prism 65b of the carriage 65, is subsequently reflected by the mirror 67 and returns on the same optical path. Finally, the reflected reference beam is coupled back into the respective optical fiber and led back to the optical coupler. The total path length of the reference beam may be adjusted by adjusting the position of the carriage 65 with respect to the linear guide 64. This allows for compensating for the back and forward movement of the head and tolerances of the headrest. In particular, the required path length in the reference arm may be about 230 mm, where the adjustment range is approximately 185-280 mm.

In the optical coupler, the reflected reference beam and the backscattered light of the measurement beam are recombined and coupled into a further optical fiber. This fiber leads to a spectrometer for analyzing the signal in a manner known as such. Suitable spectrometers are available on the market and are mounted to the base, next to the pivoting mechanism 13.

The optical unit 30 further comprises a camera 71 housed in the upper part 40, a display 75 and associated optical elements, namely a lens package 76 and a dichroic mirror 72.

Figure 6:
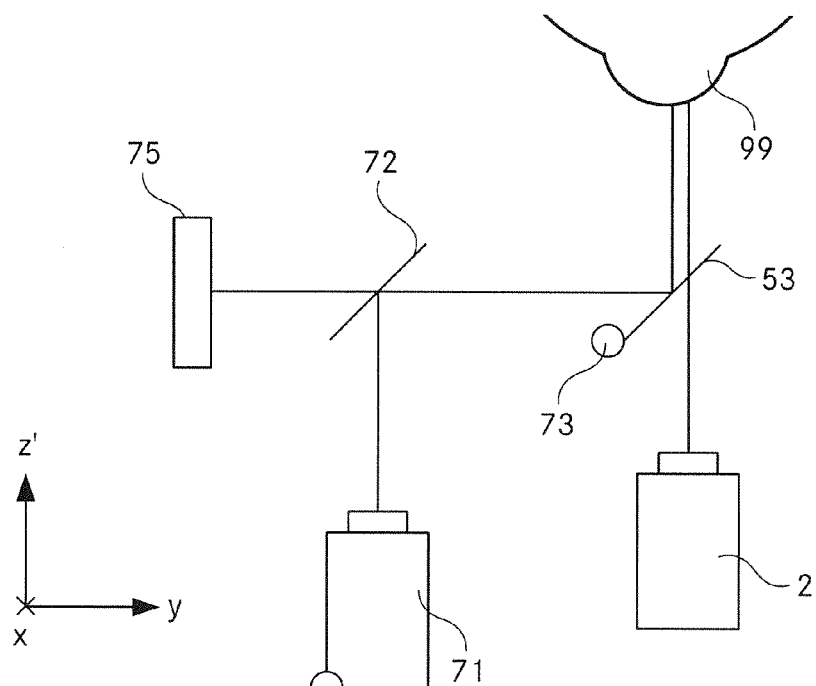
FIG. 6 the optical setup of the device for the determination of the eye position and orientation.

The optical setup is schematically shown in FIG. 6. The image shown on the display 75 is imaged by lens package 76 such that it can be perceived by the patient. The image passes the dichroic mirror 72 (shortpass, 700 nm) substantially unaffected, is reflected by the dichroic mirror 53 and enters the eye 99. For focusing purposes, the position of the display 75 may be adjusted along a linear guide 77 by means of an adjusting screw 78 rotating a spindle setting the position of the display 75 with respect to the linear guide 77.

The eye 99 is imaged by the camera 71. The eye may be illuminated by two LED light sources 73 (red, 750 nm) arranged in different positions on a frame of the dichroic mirror 53 as well as two LED light sources 74 (red, 750 nm) arranged surrounding the aperture of the camera optics. The image of the eye 99 is reflected by dichroic mirrors 53, 72 and received by camera 71. A filter may be arranged at the entry of the camera 71 in order to filter out unwanted image components, in particular coming from the display 75 and being reflected by the eye 99. In FIG. 6, the OCT is shown only schematically (reference number 2).

In the following, an example of an inventive method for the acquisition of optical coherence tomography image data of retina tissue of an eye of a human subject is described.

Figure 7:
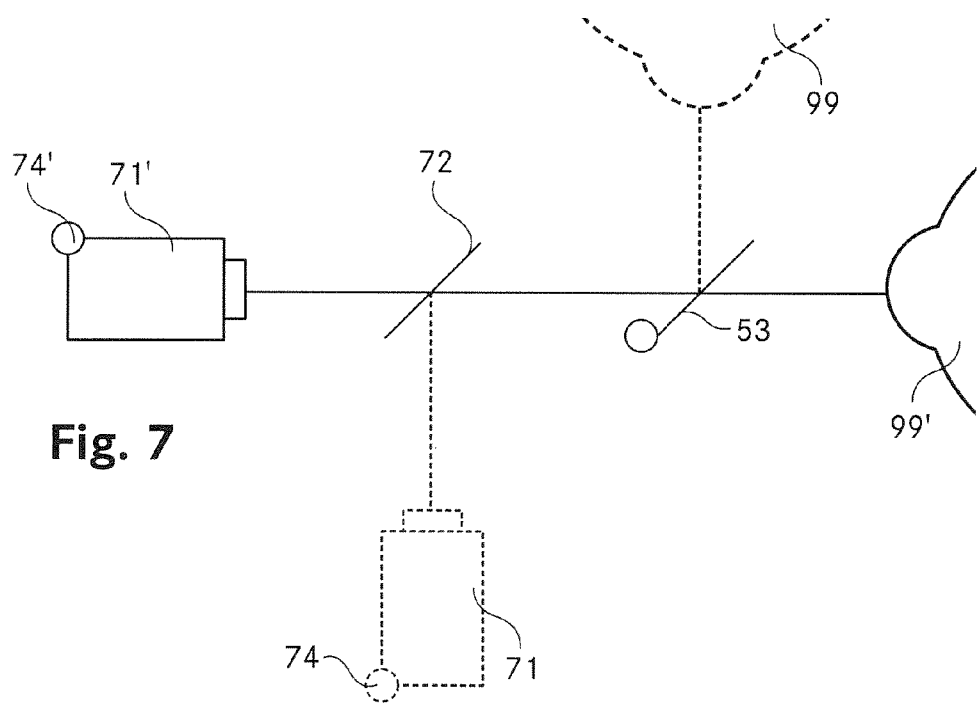
FIG. 7 a virtual scene obtained by computationally eliminating the mirrors.

For the following computations, it is advantageous to get rid of the mirrors, which reflect the light coming from the eye 99 before reaching the camera 71. For that purpose, a virtual scene is created, without any mirror, that would produce the same video image. In this virtual scene, the eye is on the right, along the y-axis, cf. FIG. 7. Since the eye is illuminated directly by the first two LEDs 73, it is required to mirror them as well, using to the following equation:

$$\begin{cases} x_{mirrored} = x - 2[(x - p_{mirror}) \cdot n_{mirror}] n_{mirror} \\ n_{mirror} = \left(0, -\sqrt{2}, \sqrt{2}\right)^t \end{cases}$$

where $p_{mirror}$ is one point on the mirror and $n_{mirror}$ is the normal to the mirror plane. An analogous transformation is performed to take care of the second mirror 72. The last two LEDs 74, on the other hand, do not illuminate the eye directly but their light is reflected by both mirrors. So in the virtual scene, they would illuminate the eye directly: they can be left as they are.

First of all, the camera needs to be calibrated. This means that a pixel location in the video image generated by the camera needs to be associated to a three-dimensional position. This allows for associating an object (a corneal reflection, a limbus point, etc.) with a location of the image plane. Camera calibration measures:
  the focal distance f (the distance between the nodal point and the image plane),
  radial and tangential distortion coefficients,
  the normalized position ($x_n$=x/y, $z'_n$=z'/y) of a 3-D object (x, y, z').

After defining the (0, 0, 0) position of the scene as the nodal point of the camera, the three-dimensional location of a projected object on the image plane is given by ($-x_n/f$, $-f$, $-z'_n/f$).

In principle, the camera may be calibrated by known algorithms and methods. As an example, the well-known open source software library OpenCV provides functionalities which allow for the determination of the above mentioned quantities on the base of an image or images of a defined test pattern, such as a tiny checkerboard.

There may be a shift between the optical axis of the OCT and that of the camera. This shift can be measured by removing the near-IR filter on the camera (and measuring the distance between the optical axis of the camera and the OCT measurement beam.

For simplicity, the nodal point of the camera is defined as the (0, 0, 0) position of the scene for the subsequent steps. The three-dimensional locations of the LEDs and that of the mirrors are fixed and therefore also known.

At the beginning of a series of acquisitions spaced in time, a reference (or baseline) image is obtained. In the context of this baseline acquisition, a patient specific calibration is undertaken. Usually, the data obtained by this calibration may be used throughout the series of acquisitions, i.e. patient specific calibration is not necessary for the subsequent image acquisitions.

Patient specific calibration aims at determining the radius(es) of corneal curvature (p) as well as the distance (r) between the center of eye rotation and the center of corneal curvature of the examined eye(s) of the human subject.

These two steps cannot be performed jointly because as shown in the following, in one case, the eye should be fixed and in the other case, it should move.

Figure 8:
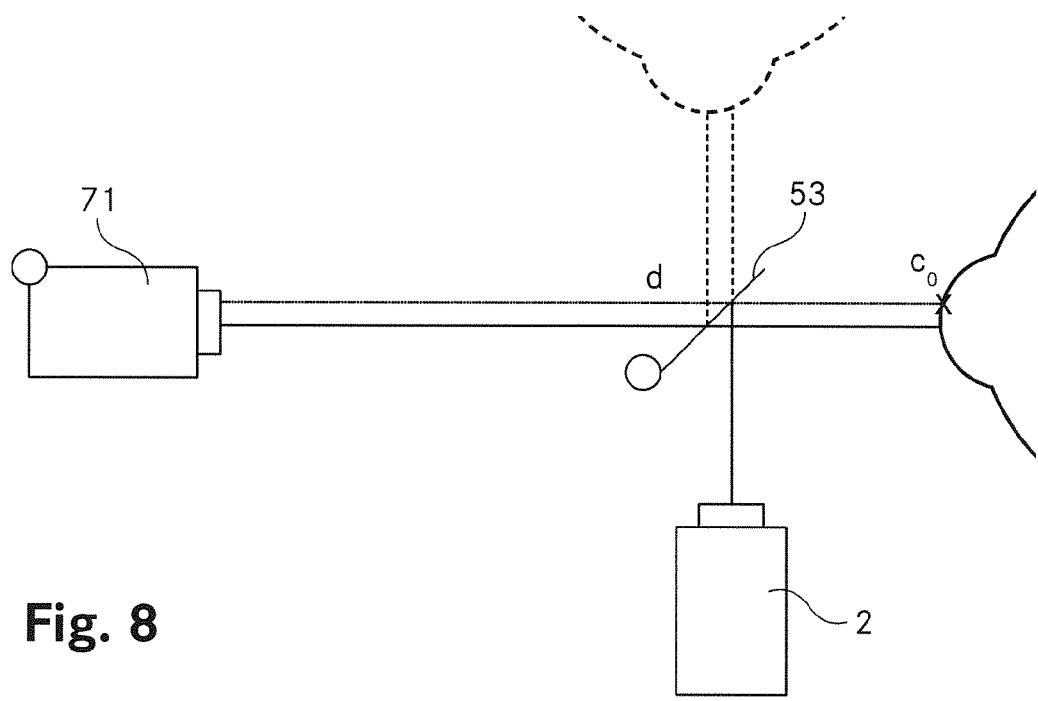
FIG. 8 the optical setup for determining the radius of corneal curvature.

For determining the radius of corneal curvature in the context of patient specific calibration, video images are recorded while the OCT tracks the cornea and sends measurements of the distance d to the eye surface. The setup is shown in FIG. 8. Once the cornea has been found, the eye should not move too much so that the OCT does not loose the cornea signal.

Once a sufficient number of images have been acquired, estimation of the size of the cornea may start. A distance measurement $d_I$ is associated with each image I. Based on these distance measurements, the coordinate of one point ($c_{I0}$) with minimal d is known on the cornea, in every image I. The radius of corneal curvature ρ can be found using the following algorithm given in pseudo-code:

```
for each ρ generated by a minimization algorithm
    σ_ρ = 0
    for each image I
        C_Iρ = center of corneal curvature
        δ_Iρ = |ρ − ||c_I0 − C_Iρ|||
        σ_ρ += δ_Iρ²
    objective: minimize σ_ρ
```

Figure 10:
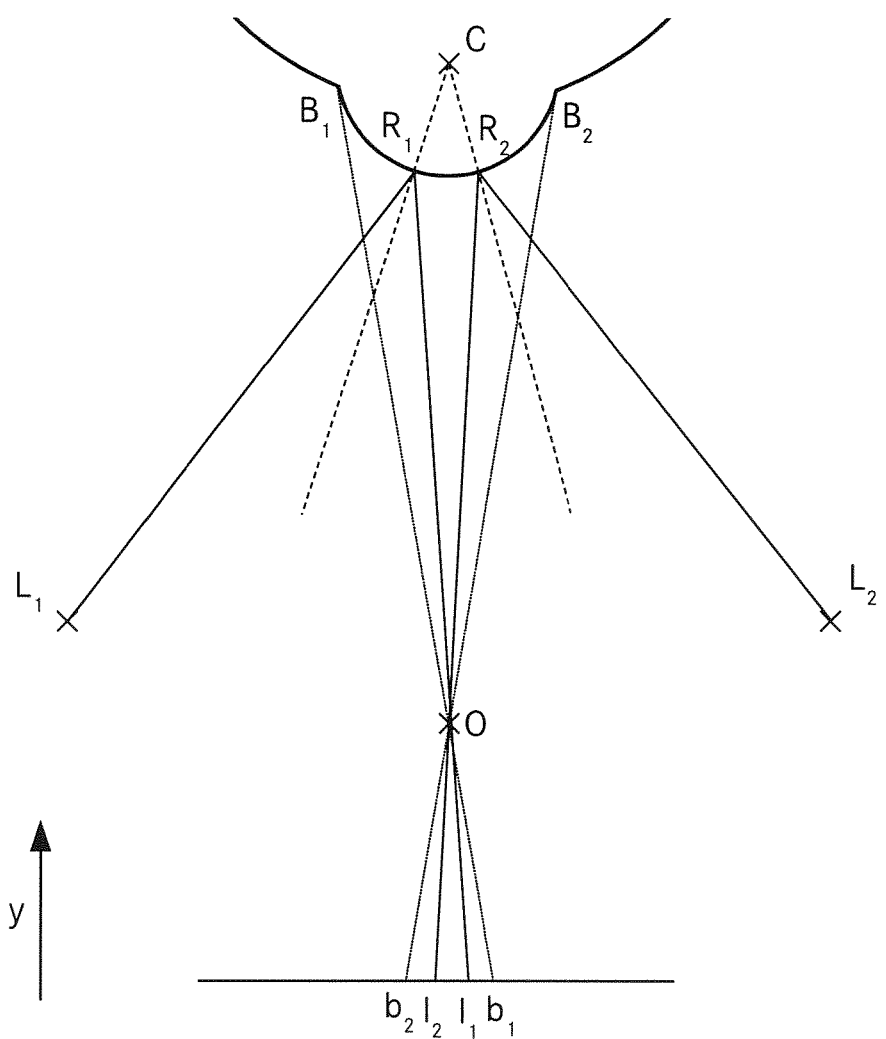
FIG. 10 the geometry for determining the eye position and orientation.

The center of corneal curvature C is shown in FIG. 10.

In practice, a soft constraint should also been added to ensure that $c_{I0}$ is between the camera and the center of corneal curvature. The simplex algorithm may be used for minimization, but a more simple solution should also work well.

Figure 9:
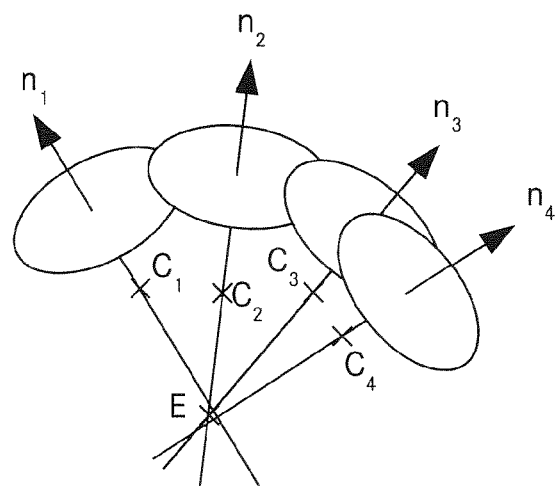
FIG. 9 the estimation of the center of eye rotation.

Next, to estimate the center of eye rotation E, the patient is asked to move the eye around while not moving the head. It is assumed that $CE_I$, the eye's optical axis in image I, is collinear to $n_I$. Therefore, E is defined as the point where all the lines directed by $n_I$ and passing through $C_I$ intersect, in the least square sense (cf. F. S. Hill Jr. *The pleasures of 'Perp Dot' products*. Ch. 11.5 in Graphics Gems IV (Ed. P. S. Heckbert). San Diego: Academic Press, pp. 138-148, 1994). This is schematically shown in FIG. 9. If the eye has moved, there will be outliers. In that case, these outliers are removed and the estimation process is run a second time.

Once the locations of the center of corneal curvature C as well as of the center of eye rotation E are known, the distance r is also known. Accordingly, the patient specific calibration is finished.

During all the acquisition processes, the baseline as well as subsequent ones, the position of the eye with respect to the imaging optics (3 Cartesian coordinates) as well as the orientation of the line of vision with respect to the imaging axis are continuously determined (i.e. established in regular or irregular intervals). The methods used for calibration purposes described above are not suitable for tracking of the eye position and orientation. However, the quantities during patient specific calibration will be used in the context of the tracking method described in the following.

In the context of the described method, the orientation of the line of vision is given by two angles only, ignoring torsion, because usual torsion angles occurring when using the acquisition device described above do not introduce critical A-scan misalignments. As described in detail below, these quantities are given by a normal vector n perpendicular to a limbus plane as well as the location of the center of eye rotation E. It is to be noted that n is not collinear to the visual axis (the FC axis, where F denotes the fovea), but rather to the optical axis (the EC axis, linking the center of corneal curvature C with the center of eye rotation E).

The corresponding determination is started by segmenting the limbus. For that purpose, the pupil is detected by well-known image processing algorithms, the pupil being defined as the darkest area, after eyelash removal. To make sure that indeed the pupil is detected, the pupil borders are segmented in a radial image: the border should be round and sharp. Moreover, the pupil should not move too much between consecutive images. Pupil detection is performed in a subsampled image.

Next, the limbus is roughly detected in a subsampled radial image centered on the pupil. A large gradient filter is used to enhance the transition between the iris and the sclera. At this point, the right and the left side of the limbus are segmented separately. Then, a line is fitted to each of these two radial segmentations. If the fitting error is high, an error is raised and a new video image will be obtained.

Next, the limbus is detected accurately in a full resolution image. The same analysis is performed again, but in a smaller region of interest. Also, this time it is checked that the two radial segmentations that are obtained, i.e. one segmentation on each side of the limbus, match. So it is tried to fit an ellipse, in the Cartesian coordinate system, to the union of both segmentations. If the fitting error is high, an error is raised, and again a new video image is obtained. Every point that deviates from the best-fit ellipse is discarded.

Next, the present position of the center of corneal curvature (C) is obtained. The eye is illuminated by the four LEDs 73, 74 emitting red light mentioned above (cf. FIG. 6), the positions of which with respect to the acquisition optics being known. The first two LEDs 73 illuminate the eye directly (i.e. without reflection on the mirror). The last two LEDs 74 are reflected on both the dichroic mirrors before reaching the eye (the direct light path is blocked). In principle, only two LEDs are required for tracking. Primarily, the first two LEDs are used, which create a larger reflection and are therefore easier to detect. The other LEDs are for backup purposes, in case one or both of the first two are not visible (if the eye if half closed for instance).

To the virtual scene as described above, some of the usual eye tracking equations (E. D. Guestrin and M. Eizenman. *General theory of remote gaze estimation using the pupil center and corneal reflections*. IEEE Trans Biomed Eng 2006; 53(6):1124-33) may be applied.

Two visible LEDs are picked and the following equations are employed to estimate the center of corneal curvature. These equations are adapted from the above mentioned paper of Guestrin/Eizenman. They are solved using a multidimensional (11-dimensional) root finding algorithm, namely the hybrid algorithm with internal scaling from the GSL library. The multidimensional root finding approach has been found to be more reliable (less sensitive to bad initialization) than multidimensional minimization, which was suggested by Guestrin/Eizenman. It is to be noted that these equations require that the radius of corneal curvature ($\rho$) is known: this parameter has been obtained in patient specific calibration as described above.

The following equations relate to finding of the center of corneal curvature, the corresponding geometry is shown in FIG. 10:

$N$ sphericity equations: $\|\overrightarrow{CR_i}\|=\rho$, $3N$ alignment equations: $\overrightarrow{R_iO}=k_i\overrightarrow{OI_i}$, $N$ incidence/reflection angle equality equations:
$$(\overrightarrow{R_iL_i}\cdot\overrightarrow{CR_i})\|\overrightarrow{R_iO}\|=(\overrightarrow{R_iO}\cdot\overrightarrow{CR_i})\|R_iL_i\|,$$

$N$ coplanarity equations: $(\overrightarrow{OL_i}\times\overrightarrow{OR_i})\cdot\overrightarrow{OC}=0$.

C denotes the center of the corneal curvature, O denotes the camera's nodal point, $L_1, \ldots, L_N$ denote the light sources, $R_1, \ldots, R_N$ the corresponding corneal reflections, $I_1, \ldots, I_N$ the corresponding images of the corneal reflections. There 4N+3 unknowns, namely C (3 components), $R_i$ (N times 3 components) and $k_i$ (N values). As there are 6N equations, in order for all unknowns being unambiguously defined, at least N=2 light sources are required.

Next, the limbus is reconstructed in three dimensions.

Now that the position of the center of corneal curvature is known, the limbus may be reconstructed in three dimensions. Based on the following equations, each pixel of the two-dimensional limbus segmentation obtained as described above may be mapped to a three-dimensional location on the actual limbus. This reconstruction uses the fact that the limbus is somewhere on the cornea ball. The same multidimensional (in this case 4-dimensional) root finding algorithm was used to reconstruct the limbus.

The following equations relate to finding each limbus point (4 equations, 4 unknowns).

1 sphericity equation: $\|\overrightarrow{CB_i}\|=\rho$, 3 alignment equations: $\overrightarrow{B_iO}=k'_i\overrightarrow{Ob_i}$, where $B_1, \ldots, B_M$ denote points on the limbus, $b_1, \ldots, b_M$ images of the limbus points, and $\rho$ denotes the radius of corneal curvature.

Once the limbus has been reconstructed in three dimensions, the next step is to find the normal n to the "limbus plane". This can be done by fitting a plane to the limbus 3-D point cloud ($B_1, B_2, \ldots, B_M$). For that purpose, a three-dimensional singular value decomposition of the following matrix is performed:

$$X = \begin{bmatrix} (B_1 - \text{average}(B_i))^t \\ (B_2 - \text{average}(B_i))^t \\ \vdots \\ (B_M - \text{average}(B_i))^t \end{bmatrix}$$

The normal to the best-fit plane is given by the third eigenvector of X, that is the one associated with the smallest eigenvalue. The unit vector n is defined to be this normal, or its opposite: the multiplicative sign (1 or −1) is chosen such that n is directed towards the center of corneal curvature C, i.e. such that n·C>0.

Finally, the center of eye rotation E is estimated by the following formula:

$$E=C+rn.$$

The distance r between the center of corneal curvature C and the center of eye rotation E has been estimated during patient specific calibration as described above. It is to be noted that EC and n are considered to be collinear, which is usually reasonable but might not always be true.

During the acquisition of the reference (or baseline) image, the relative positioning of the eye with respect to the imaging optics is stored, either on the imaging device, an external data carrier or a central server connected to the imaging device. When acquiring further images the eye and the imaging optics shall have the same relative positioning. When comparing the two images, this allows for neglecting various optical effects that are due to the specific relative positioning. Especially in the case where the images are analyzed automatically, by a corresponding algorithm, it is usually required that the images to be compared to each other show the same view of the same region of tissue, this includes e.g. that the views have the same viewing angle and the same size. In principle, this may be achieved by post-processing at least one of the acquired images. However, this introduces a certain error and requires a considerable amount of processing power. According to the invention, the postprocessing may be minimized or even dispensed with, due to the fact, that the two images will always show the same view.

In order to achieve that, the present relative position and orientation determined as described above is constantly compared with the stored relative positioning. As soon as the difference between the two is within a narrow window, the acquisition of an OCT scan will be triggered.

In the context of the described embodiment, the correct relative positioning in space may be obtained by correspondingly pivoting the optical unit about the x and y axes as well as linearly moving the optical unit along the z' axis until the stored relative positioning with respect to the relative positions is reached. A rough starting position may be set based on the stored data, due to the fact that the position of the head support is substantially fixed with respect to the base of the device. The fine positioning is based on a comparison of the stored values with the value of the center of eye rotation E and corresponding adjustments. If the eye of the patient moves, the positioning of the optical unit is automatically readjusted.

It remains the relative orientation. This is achieved by the human subject accordingly changing its line of vision. In order to motivate the human subject to move his or her eye, a target image is shown to the human subject, the target image indicating a direction of a line of vision to be assumed by the human subject. As an example, the target image may be a group of arrows pointing to the desired direction as long as the orientation (given by the unit vector n) does not match the stored value. As soon as the value is matched, the acquisition is triggered and simultaneously, the arrows are replaced e.g. by circles or crosses, i.e. shapes that do not mark a certain direction.

The invention is not restricted to the method described above, and an inventive method may be carried out on devices that are different from that described above.

In summary, it is to be noted that the invention provides a method for the acquisition of OCT image data as well as an OCT imaging device pertaining to the technical field initially mentioned, that are inexpensive and allow for reliable positioning of the eye to be examined.

The invention claimed is:

1. A method for the acquisition of optical coherence tomography image data of retina tissue of an eye of a human subject using an acquisition device comprising an imaging optics, comprising the steps of:
   a) at a first point in time acquiring a first image associated with a baseline relative positioning of the eye of the human subject with respect to the imaging optics;
   b) storing the baseline relative positioning;
   c) at a second point in time being different from the first point in time, re-establishing the baseline relative positioning of the same eye of the same human subject with respect to the imaging optics, and acquiring a second image, where
   d) for re-establishing the positioning, a present relative positioning of the eye of the human subject with respect to the imaging optics is determined based on a video image of an iris region of the eye, the determination comprising the step of determining a three-dimensional position and an orientation of the eye,
   e) the re-establishing step includes displaying a target image to the human subject, the target image indicating a direction of a line of vision to be assumed by the human subject, and
   f) a present relative positioning of the eye of the human subject with respect to the imaging optics is compared to the stored baseline relative positioning, the displayed target image is affected as long as the present relative positioning does not correspond to the stored baseline relative positioning, and the second image is acquired when the present relative positioning corresponds to the baseline relative positioning.

2. The method as recited in claim 1, characterized in that the re-establishing step includes an automated repositioning of the imaging optics.

3. The method as recited in claim 2, characterized in that a head of the human subject is held in a fixed position with respect to a base of the acquisition device and in that for repositioning the imaging optics is moved with respect to the base.

4. The method as recited in claim 1, characterized in that a position of a limbus cornae in the video image is determined and used as a reference for the present relative positioning of the eye.

5. The method as recited in claim 1, characterized in that the three-dimensional position and the orientation of the eye are determined by identifying the following quantities:
   a) a center of eye rotation; and
   b) a normal vector to a limbus plane.

6. The method as recited in claim 1, characterized in that the determination of the present relative positioning of the eye with respect to the imaging optics comprises the step of determining a center of corneal curvature based on reflected light rays of at least two light sources illuminating the eye, the at least two light sources being spaced from each other.

7. The method as recited in claim 1, characterized by the step of determining a radius of corneal curvature of the eye of the human subject by recording video images, simultaneously acquiring OCT images of the cornea to determine a distance of the cornea from the imaging optics, assigning distance values to locations of the video image and determining the radius by a numerical optimization algorithm.

8. The method as recited in claim 1, characterized by the step of determining a distance of the center of eye rotation and a center of corneal curvature of the eye of the human subject.

9. A device for the acquisition of optical coherence tomography image data of retina tissue of an eye of a human subject, comprising
   a) an imaging optics;
   b) a head support to be contacted by a head portion of the human subject, the head support defining an entrance position of the sample beam entering an eye of the human subject;
   c) a camera for acquiring a video image of an iris region of the eye;
   d) a display for displaying a target image to the human subject, the target image indicating a direction of a line of vision to be assumed by the human subject;

e) a processor for determining a present relative positioning of the eye of the human subject with respect to the imaging optics, based on the video image, the determination comprising the step of determining a three-dimensional position and an orientation of the eye, for comparing a present relative positioning of the eye of the human subject with respect to the imaging optics to a stored baseline relative positioning, for affecting the target image as long as the present relative positioning does not correspond to the stored baseline relative positioning, and for triggering the acquisition of image data when the present relative positioning corresponds to the baseline relative positioning.

10. The device as recited in claim 9, characterized in that the device comprises a base, the head support being fixed to the base and the imaging optics being movable with respect to the base.

11. The device as recited in claim 10, characterized by an adjustment mechanism for automatically three-dimensionally adjusting a position of the imaging optics with respect to the base.

\* \* \* \* \*